United States Patent [19]

Strube et al.

[11] Patent Number: 5,455,181
[45] Date of Patent: Oct. 3, 1995

[54] THROMBIN-INHIBITORY PROTEINS FROM TERRESTRIAL LEECHES

[75] Inventors: Karl-Hermann Strube, Speyer; Siegfried Bialojan, Oftersheim; Burkhard Kroeger, Limburgerhof; Thomas Friedrich, Darmstadt, all of Germany

[73] Assignee: BASF Aktiengesellschaft, Ludwigshafen, Germany

[21] Appl. No.: 244,113

[22] PCT Filed: Nov. 19, 1992

[86] PCT No.: PCT/EP92/02661

§ 371 Date: May 18, 1994

§ 102(e) Date: May 18, 1994

[87] PCT Pub. No.: WO93/11239

PCT Pub. Date: Oct. 6, 1993

[30] Foreign Application Priority Data

Nov. 26, 1991 [DE] Germany ............. 41 38 698.1
Mar. 20, 1992 [DE] Germany ............. 42 09 110.1

[51] Int. Cl.[6] ............. C12N 15/00; C12P 21/06; A61K 38/00; C07K 1/00
[52] U.S. Cl. ............. 435/320.1; 435/69.1; 435/240.2; 435/252.3; 514/2; 514/12; 530/300; 530/324; 536/22.1; 536/23.1; 536/23.5
[58] Field of Search ............. 435/69.1, 240.2, 435/252.3, 320.1; 514/2, 12; 530/300, 324; 536/22.1, 23.1, 23.5

[56] References Cited

FOREIGN PATENT DOCUMENTS 142860 11/1984 European Pat. Off. .
168342 6/1985 European Pat. Off. .

OTHER PUBLICATIONS

Primary structures of new 'iso–hirudins, Scharf et al. Febs Letters, vol. 255, No. 1, Sep. 1989.

*Primary Examiner*—Robert A. Wax
*Assistant Examiner*—Hyosuk Kim
*Attorney, Agent, or Firm*—Keil & Weinkauf

[57] ABSTRACT

Novel thrombin-inhibitory proteins from terrestrial leeches of the genus Haemadipsa with the amino-acid sequence Ile-Arg-Phe-Gly-Met-Gly-Lys-Val-Pro-Cys-Pro-Asp- Gly-Glu-Val-Gly-Tyr-Thr-Cys-Asp-Cys-Gly-Glu-Lys-Ile-Cys-Leu-Tyr-Gly-Gln-Ser-Cys-Asn-Asp-Gly-Gln-Cys-Ser-Gly-Asp- Pro-Lys-Pro-Ser-Ser-Glu-Phe-Glu-Glu-Phe-Glu-Ile-Asp-Glu- Glu-Glu-Lys, or an amino-acid sequence which is obtained by C-terminal truncation of this sequence by from one to twelve amino acids, are described. The proteins are suitable for controlling diseases. Also described are the nucleic acids coding for these proteins.

7 Claims, 4 Drawing Sheets

SEQUENCE LISTING ( 1 ) GENERAL INFORMATION:

( i i i ) NUMBER OF SEQUENCES: 23

( 2 ) INFORMATION FOR SEQ ID NO: 1:

( i ) SEQUENCE CHARACTERISTICS:
( A ) LENGTH: 57 amino acids
( B ) TYPE: amino acid ( D ) TOPOLOGY: linear ( x i ) SEQUENCE DESCRIPTION: SEQ ID NO: 1:

```
Ile Arg Phe Gly Met Gly Lys Val Pro Cys Pro Asp Gly Glu Val Gly
 1               5                  10                  15

Tyr Thr Cys Asp Cys Gly Glu Lys Ile Cys Leu Tyr Gly Gln Ser Cys
                20                  25                  30

Asn Asp Gly Gln Cys Ser Gly Asp Pro Lys Pro Ser Ser Glu Phe Glu
            35                  40                  45

Glu Phe Glu Ile Asp Glu Glu Lys
        50                  55
```

( 2 ) INFORMATION FOR SEQ ID NO: 2:

( i ) SEQUENCE CHARACTERISTICS:
( A ) LENGTH: 45 amino acids
( B ) TYPE: amino acid
( D ) TOPOLOGY: linear ( x i ) SEQUENCE DESCRIPTION: SEQ ID NO: 2:

```
Ile Arg Phe Gly Met Gly Lys Val Pro Cys Pro Asp Gly Glu Val Gly
 1               5                  10                  15

Tyr Thr Cys Asp Cys Gly Glu Lys Ile Cys Leu Tyr Gly Gln Ser Cys
                20                  25                  30

Asn Asp Gly Gln Cys Ser Gly Asp Pro Lys Pro Ser Ser
            35                  40                  45
```

( 2 ) INFORMATION FOR SEQ ID NO: 3:

( i ) SEQUENCE CHARACTERISTICS:
( A ) LENGTH: 44 amino acids
( B ) TYPE: amino acid
( D ) TOPOLOGY: linear ( x i ) SEQUENCE DESCRIPTION: SEQ ID NO: 3:

```
Ile Arg Phe Gly Met Gly Lys Val Pro Cys Xaa Xaa Gly Glu Val Gly
 1               5                  10                  15

Tyr Thr Cys Asp Cys Gly Xaa Xaa Ile Cys Leu Tyr Gly Gln Ser Cys
                20                  25                  30

Asn Asp Gly Gln Cys Ser Gly Asp Pro Lys Pro Ser
            35                  40
```

( 2 ) INFORMATION FOR SEQ ID NO: 4:

( i ) SEQUENCE CHARACTERISTICS:
( A ) LENGTH: 25 amino acids
( B ) TYPE: amino acid
( D ) TOPOLOGY: linear ( x i ) SEQUENCE DESCRIPTION: SEQ ID NO: 4:

```
Ile Arg Phe Gly Met Gly Lys Val Pro Cys Pro Asp Gly Glu Val Gly
 1               5                  10                  15

Tyr Thr Cys Asp Cys Gly Glu Xaa Ile
                20                  25
```

( 2 ) INFORMATION FOR SEQ ID NO: 5:

( i ) SEQUENCE CHARACTERISTICS:
( A ) LENGTH: 43 amino acids
( B ) TYPE: amino acid
( D ) TOPOLOGY: linear ( x i ) SEQUENCE DESCRIPTION: SEQ ID NO: 5:

Ile Arg Phe Gly Met Gly Lys Val Pro Xaa Pro Asp Gly Glu Val Gly
1               5                       10                      15

Tyr Thr Xaa Asp Xaa Gly Glu Lys Ile Xaa Leu Tyr Gly Gln Ser Xaa
            20                      25                      30

Asn Asp Gly Gln Xaa Ser Gly Asp Pro Lys Xaa
            35                      40

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( D ) TOPOLOGY: linear ( x i ) SEQUENCE DESCRIPTION: SEQ ID NO: 6:

Ile Xaa Phe Gly Met Gly Lys Val Pro Cys Pro Asp Gly Glu Val Gly
1               5                       10                      15

Tyr Thr Cys Asp Cys Gly Xaa Xaa Ile
            20                      25

( 2 ) INFORMATION FOR SEQ ID NO: 7:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO: 7:

Ile Xaa Phe Gly Met Gly Lys Val Pro Cys Leu Asp Gly Glu Val Gly
1               5                       10                      15

Tyr ( 2 ) INFORMATION FOR SEQ ID NO: 8:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO: 8:

Val Pro Cys Pro Asp Gly Glu Val Gly Tyr Thr Cys Asp Cys Gly
1               5                       10                      15

( 2 ) INFORMATION FOR SEQ ID NO: 9:

( i ) SEQUENCE CHARACTERISTICS:
        ( A ) LENGTH: 20 amino acids
        ( B ) TYPE: amino acid
        ( D ) TOPOLOGY: linear ( x i ) SEQUENCE DESCRIPTION: SEQ ID NO: 9:

Val Pro Cys Pro Asp Gly Glu Val Gly Tyr Thr Cys Asp Cys Gly Xaa
1               5                       10                      15

Asn Ile Cys Leu
            20

( 2 ) INFORMATION FOR SEQ ID NO: 10:

( i ) SEQUENCE CHARACTERISTICS:
        ( A ) LENGTH: 22 amino acids
        ( B ) TYPE: amino acid
        ( D ) TOPOLOGY: linear ( x i ) SEQUENCE DESCRIPTION: SEQ ID NO: 10:

```
Ile Cys Leu Tyr Gly Gln Ser Cys Asn Asp Gly Gln Cys Ser Gly Asp
 1               5                   10                  15
Pro Lys Pro Ser Ser Xaa
            20
```

( 2 ) INFORMATION FOR SEQ ID NO: 11:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO: 11:

```
Gly Met Gly Lys Val Pro Cys Pro
 1               5
```

( 2 ) INFORMATION FOR SEQ ID NO: 12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

GGAATGGGNA ARGTNCCNTG YCC                                                23

( 2 ) INFORMATION FOR SEQ ID NO: 13:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO: 13:

```
Cys Asp Cys Gly Glu Lys Ile Cys
 1               5
```

( 2 ) INFORMATION FOR SEQ ID NO: 14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

TGYGAYTGYG GNGARAARAT HTG                                                23

( 2 ) INFORMATION FOR SEQ ID NO: 15:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

CGAGGGGGAT GGTCGACGGA AGCGACCTTT TTTTTTTTTT TTTTT                     45

( 2 ) INFORMATION FOR SEQ ID NO: 16:

( i ) SEQUENCE CHARACTERISTICS:
        ( A ) LENGTH: 19 base pairs
        ( B ) TYPE: nucleic acid
        ( C ) STRANDEDNESS: single

5,455,181

17

18

-continued ( D ) TOPOLOGY: linear ( x i ) SEQUENCE DESCRIPTION: SEQ ID NO: 16:

CGAGGGGAT GGTCGACGG                                                                                                19

( 2 ) INFORMATION FOR SEQ ID NO: 17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

GATGGTCGAC GGAAGCGACC                                                                                              20

( 2 ) INFORMATION FOR SEQ ID NO: 18:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 18:

```
TGT  GAT  TGT  GGT  GAA  AAG  ATA  TGT  TTG  TAT  GGA  CAA  AGC  TGC  AAT  GAT         48
Cys  Asp  Cys  Gly  Glu  Lys  Ile  Cys  Leu  Tyr  Gly  Gln  Ser  Cys  Asn  Asp
 1              5                        10                       15

GGT  CAA  TGC  TCA  GGT  GAT  CCT  AAA  CCA  AGC  AGT  GAA  TTC  GAA  GAA  TTT         96
Gly  Gln  Cys  Ser  Gly  Asp  Pro  Lys  Pro  Ser  Ser  Glu  Phe  Glu  Glu  Phe
               20                       25                       30

GAA  ATT  GAT  GAA  GAA  GAA  AAA  TAATTATTAA TATTTCCTAG TATCTCTAGT                    147
Glu  Ile  Asp  Glu  Glu  Glu  Lys
           35
```

ACAATTGTTA GCTTTGGCAA TAATTATCTG TAACAAATGA ATTGTTTGAA AAATAATAAA                      207

GAATTATTAT TATTGATGAC AAAAAAAAAA AAAAAAAAAA AAAAAAAAAA GGTCGCTTCC                      267

GTCGACCATC                                                                             277

( 2 ) INFORMATION FOR SEQ ID NO: 19:

( i ) SEQUENCE CHARACTERISTICS:
        ( A ) LENGTH: 39 amino acids
        ( B ) TYPE: amino acid
        ( D ) TOPOLOGY: linear ( x i ) SEQUENCE DESCRIPTION: SEQ ID NO: 19:

```
Cys  Asp  Cys  Gly  Glu  Lys  Ile  Cys  Leu  Tyr  Gly  Gln  Ser  Cys  Asn  Asp
 1              5                        10                       15

Gly  Gln  Cys  Ser  Gly  Asp  Pro  Lys  Pro  Ser  Ser  Glu  Phe  Glu  Glu  Phe
               20                       25                       30

Glu  Ile  Asp  Glu  Glu  Glu  Lys
           35
```

( 2 ) INFORMATION FOR SEQ ID NO: 20:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 20:

GGGGGGGTCG ACGGATCCGT TACAGATAAT TATTGCCAAA GC                                          42

( 2 ) INFORMATION FOR SEQ ID NO: 21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 21:

```
CAGGAAACAG CTATGACC                                                              18
```

( 2 ) INFORMATION FOR SEQ ID NO: 22:

( i ) SEQUENCE CHARACTERISTICS:
        ( A ) LENGTH: 353 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 22:

```
ATTTAGTTAA TTTTATTCTG CTTTGAAAGA ATTGCTGAAG ATG TTC TCA ACA AAG                  55
                                             Met Phe Ser Thr Lys
                                             -20

ATG TTT GTT GTT TTT GTT GCA GTT TGC ATC TGC GTA ACT CAG TCT ATA                 103
Met Phe Val Val Phe Val Ala Val Cys Ile Cys Val Thr Gln Ser Ile
-15              -10                  -5                         1

AGA TTT GGA ATG GGC AAA GTT CCA TGC CCA GAT GGC GAA GTG GGA TAC                 151
Arg Phe Gly Met Gly Lys Val Pro Cys Pro Asp Gly Glu Val Gly Tyr
             5                   10                  15

ACT TGC GAC TGT GGG GAA AAG ATT TGT TTG TAT GGA CAA AGC TGC AAT                 199
Thr Cys Asp Cys Gly Glu Lys Ile Cys Leu Tyr Gly Gln Ser Cys Asn
         20                  25                  30

GAT GGT CAA TGC TCA GGT GAT CCT AAA CCA AGC AGT GAA TTC GAA GAA                 247
Asp Gly Gln Cys Ser Gly Asp Pro Lys Pro Ser Ser Glu Phe Glu Glu
     35                  40                  45

TTT GAA ATT GAT GAA GAA GAA AAA TAATTATTAA TATTTCCTAG TATCTCTAGT                301
Phe Glu Ile Asp Glu Glu Glu Lys
50                  55

ACAATTGTTA GCTTTGGCAA TAATTATCTG TAACGGATCC GTCGACCCCC CC                       353
```

( 2 ) INFORMATION FOR SEQ ID NO: 23:

( i ) SEQUENCE CHARACTERISTICS:
        ( A ) LENGTH: 77 amino acids
        ( B ) TYPE: amino acid
        ( D ) TOPOLOGY: linear ( x i ) SEQUENCE DESCRIPTION: SEQ ID NO: 23:

```
Met Phe Ser Thr Lys Met Phe Val Val Phe Val Ala Val Cys Ile Cys
-20                  -15                 -10                  -5

Val Thr Gln Ser Ile Arg Phe Gly Met Gly Lys Val Pro Cys Pro Asp
                 1                   5                  10

Gly Glu Val Gly Tyr Thr Cys Asp Cys Gly Glu Lys Ile Cys Leu Tyr
             15                  20                  25

Gly Gln Ser Cys Asn Asp Gly Gln Cys Ser Gly Asp Pro Lys Pro Ser
         30                  35                  40

Ser Glu Phe Glu Glu Phe Glu Ile Asp Glu Glu Glu Lys
     45                  50                  55
```

THROMBIN-INHIBITORY PROTEINS FROM TERRESTRIAL LEECHES

FIELD OF THE INVENTION

The present invention relates to novel thrombin-inhibitory proteins from the terrestrial leech Haemadipsa sylvestris and to processes for the preparation thereof.

BACKGROUND OF THE INVENTION

Thrombin inhibitors are important therapeutic substances used, for example, for the prophylaxis or treatment of thromboses or arterial reocclusions.

EP 142 860 describes the thrombin inhibitor hirudin from the medical leech (Hirudo medicinalis) with its primary structure. Furthermore, the preparation of hirudin by genetic manipulation is disclosed, for example, in EP 168 342.

SUMMARY OF THE INVENTION

We have now found novel thrombin-inhibitory proteins from the terrestrial leech Haemadipsa sylvestris.

The novel proteins have the following physicochemical properties. A molecular weight of 11200± 1000 dalton is assigned to them by molecular sieve chromatography. A molecular weight of 5000±1000 dalton is determined in an SDS polyacrylamide gel.

The proteins bind specifically to a thrombin affinity column. They inhibit the biological activity of thrombin in an in vitro enzyme assay.

The following N-terminal amino-acid sequence was determined for the proteins (SEQ ID NO: 3): Ile-Arg-Phe-Gly-Met-Gly-Lys-Val-Pro-Cys-D-A-Gly-Glu-Val- Gly-Tyr-Thr-Cys-Asp-Cys-Gly-B-C-Ile-Cys-Leu-Tyr-Gly-Gln- Ser-Cys-Asn-Asp-Gly-Gln-Cys-Ser-Gly-Asp-Pro-Lys-Pro-Ser, where A is Asp or Phe, B is Glu or Trp, C is Lys, Asn or Asp, and D is Pro or Leu.

The novel proteins can be isolated from terrestrial leeches of the genus Haemadipsa. For this, the leeches are expediently homogenized in a buffer at pH 6–9, preferably pH 7–8, in a homogenizer, preferably a mixer. The insoluble constituents are then removed, preferably by centrifugation.

The proteins can be further purified from the resulting solution by chromatographic methods, preferably ion exchange chromatography and/or affinity chromatography. A purification step by thrombin affinity chromatography is particularly preferred.

After affinity chromatography on a thrombin column it is possible to separate various isoproteins with thrombin-inhibitory activity by reversed phase HPLC (see FIG. 1).

The purification of the proteins can be followed by a thrombin activity assay. It is expedient to use for this an optical assay in which a chromogenic substrate, for example Chromozym TH, is converted by thrombin. The fractions containing the novel proteins can be identified on addition to this optical assay by their thrombin-inhibiting action.

Genetic manipulation processes are particularly suitable for preparing the proteins according to the invention.

To do this, a leech cDNA gene bank is set up in a conventional way. The gene coding for the protein according to the invention can be isolated from this gene bank by, for example, preparing a DNA probe whose sequence is obtained from the N-terminal amino-acid sequence described above by translation back in accordance with the genetic code. The appropriate gene can be found and isolated by hybridization with this DNA probe.

However, the polymerase chain reaction (PCR) technique can also be employed to prepare the appropriate gene. For example, it is possible with the aid of a primer whose sequence has been obtained by translation back from the N-terminal amino-acid sequence described above, and of a second primer whose sequence is complementary to the 3' end of the cDNA gene fragment, preferably with the sequence poly(dT), to prepare the cDNA gene fragment for the protein according to the invention by the PCR technique. The appropriate gene can also be isolated by setting up a leech expression gene bank and screening it with an antibody directed against the protein according to the invention.

A cDNA which codes for a protein according to the invention is depicted in SEQ ID NO: 22.

Other suitable DNA sequences are those which, although their nucleotide sequence differs from that detailed in SEQ ID NO: 22, do code, as a consequence of the degeneracy of the genetic code, for the polypeptide chain detailed in SEQ ID NO: 22, or parts thereof. Also suitable are those DNA sequences which code for proteins with thrombin-inhibitory action and which hybridize under standard conditions with the nucleotide sequence depicted in SEQ ID NO: 22 or with a nucleotide sequence which codes for the protein depicted in SEQ ID NO: 22. The experimental conditions for DNA hybridization are described in textbooks of genetic manipulation, for example in Maniatis et al., Molecular Cloning, Cold Spring Harbor Laboratory, 1990.

Standard conditions mean, for example, an aqueous buffer solution with a concentration of from 0.1 to 1×SSC (1×SSC: 0.15 M NaCl, 15 mM sodium citrate, pH 7.2) at from 42° to 58° C.

Once the appropriate gene has been isolated it can be expressed by processes of genetic manipulation in organisms, eg. in bacteria, yeasts or higher eukaryotic cells, with the aid of an expression vector in a conventional way.

It is preferable to use prokaryotic expression systems which synthesize the proteins according to the invention in the form of fusion proteins. An example of an expression system of this type is the commercially available Profusion* system (New England Biolabs) which synthesizes the required protein as fusion protein with the maltose binding protein under the control of the inducible tac promoter.

The required protein can be liberated from the fusion protein by cleavage with factor Xa.

The protein can be isolated from these recombinant host systems on the basis of the physicochemical properties described above.

The general procedure for the preparation of a novel protein with a known partial amino-acid sequence by genetic manipulation is described in textbooks of genetic engineering, for example E. L. Winnacker, Gene und Klone, Verlag Chemie, Weinheim, 1984. The experimental conditions for the individual processes such as, for example, setting up a gene bank, hybridization expression of a gene, are described by T. Manniatis, Molecular Cloning, Cold Spring Harbor Laboratory, 1990.

The cDNA sequence described in SEQ ID NO: 22 provides the possibility of mutating the protein encoded thereby with the aid of conventional methods. These make it possible to prepare proteins in which individual amino acids in the protein sequence indicated in SEQ ID NO: 22 have been replaced. Particularly well suited proteins are those which are obtained by modifications of the ends of the polypeptides, in particular by truncations of the ends. Particularly well suited proteins are obtainable by truncations of the C terminus, preferably by from one to twelve amino acids. The muteins truncated in this way likewise have a thrombin-inhibitory action.

The proteins according to the invention are preferably used in the form of their pharmaceutically acceptable salts.

The novel proteins have anticoagulant properties. They can be used, for example, for the prophylaxis of thromboses or arterial reocclusions, for the treatment of thromboses, for preserving blood or for extracorporeal circulation.

The novel proteins are effective thrombin inhibitors. They can be used alone or else together with known anticoagulant factors as drugs. Anticoagulant factors which are preferably used are thrombin inhibitors, for example hirudin, factor Xa inhibitors, for example TAP (Waxman et al., Science 248 (1990) pp. 593–596) or platelet aggregation inhibitors, for example Kistrin (Dennis et al., Proc. Natl. Acad. Sci. USA 87 (1989) pp. 2471–2475).

DESCRIPTION OF THE PREFERRED EMBODIMENTS

The invention is illustrated further by the following examples.

EXAMPLE 1

Purification of the thrombin-inhibitory proteins from terrestrial leeches a) Obtaining leech homogenates 150 g of live terrestrial leeches (Haemadipsa sylvestris) were homogenized in 400 ml of 20 mM sodium phosphate buffer (pH 7.4) with a mixer at 4° C. for 10 minutes. The homogenate was centrifuged at 2000 rpm (Sorvall RC-5B, Rotor GS-3) for 15 minutes and then, after removal of the precipitate, at 8000 rpm for 30 minutes. The precipitate was discarded, and the supernatant was diluted with 50 mM tris(hydroxymethyl)aminomethane/HCl buffer pH 8.5 (tris/HCl buffer) to a volume of about 600 ml.

The protein solution had a volume of 580 ml, the protein concentration was 4.49 mg/ml and the thrombin-inhibiting activity was 22.2 U/ml.

b) Fractionation of terrestrial leech homogenates by ion exchange chromatography The protein solution obtained from the leech homogenates was loaded onto a Q-Sepharose® column (50–70 ml, 2.5 cm diameter) equilibrated with 50 mM tris/HCl buffer pH 8.5. After unbound material had been washed out with the equilibration buffer, the bound proteins were eluted with a gradient of 0–1 M NaCl in 20 mM tris/HCl pH 8.5. Fractions of about 7 ml were collected and examined for protein content and thrombin-inhibitory activity (Table 1). Fractions containing thrombin-inhibitory activity were combined.

TABLE 1

| SEPARATION ON Q-SEPHAROSE® | | | | | |
|---|---|---|---|---|---|
| | Loaded | Flow-through | $P_1$ | $P_2$ | $P_3$ |
| Volume [ml] | 580 | 580 | 160 | 110 | 130 |

TABLE 1-continued

| SEPARATION ON Q-SEPHAROSE® | | | | | |
|---|---|---|---|---|---|
| | Loaded | Flow-through | $P_1$ | $P_2$ | $P_3$ |
| Protein concentration [mg/ml] | 4.5 | 1.18 | 1.46 | 5.87 | 0.48 |
| Antithrombin activity [U/ml] | 22.2 | — | — | 78 | 6.5 | c) Isolation of proteins with thrombin-inhibitory activity by affinity chromatography Product fractions from the Q-Sepharose® column were diluted 1:2 with 20 mM phosphate buffer pH 7.5 and loaded onto a thrombin-Sepharose column (preparation described in Example 3). After unbound proteins had been removed, the column was first washed with 10 column volumes of 20 mM phosphate buffer, 500 mM NaCl pH 7.5. This removed any non-specifically adsorbed proteins. Subsequently, the specifically bound thrombin inhibitors were eluted with 100 mM glycine/HCl pH 2.8. The thrombin-inhibiting activity in the eluates was determined, and the product fractions were combined (Table 2). After concentration using a 3000 D membrane (Filtron Omega Alpha Cat. No. AM003062), the concentrate was evaporated to dryness in a vacuum evaporator.

TABLE 2

| SEPARATION ON THROMBIN-SEPHAROSE | | | | | |
|---|---|---|---|---|---|
| | Loaded | Flow-through | $P_1$ | $P_2$ | $P_3$ |
| Volume [ml] | 390 | 390 | 21 | 8 | 12 |
| Protein concentration [mg/ml] | 1.47 | 1.18 | 0.03 | — | 0.035 |
| Antithrombin activity [U/ml] | 15.1 | 2 | 36 | 30 | 250 | d) Purification of the thrombin inhibitors by reversed phase HPLC

The product fraction ($P_3$) from the thrombin-Sepharose chromatography was dissolved in 0.1% by weight trifluoroacetic acid (TFA) in $H_2O$ and loaded onto a reversed phase HPLC column (BioRad rp304®). After the column had been washed with 0.1% by weight TFA in water for 5 minutes, fractionation was carried out with a linear gradient from 0.1% by weight TFA in water to 0.1% by weight TFA in acetonitrile at 1%/min (FIG. 1). The proteins eluted from the HPLC column were detected by UV at 210 nm and fractionated. The thrombin-inhibiting activity present in the individual fractions was determined after removal of the solvent and resuspension in water (0.2 ml) (Table 3).

TABLE 3

| SEPARATION BY REVERSED PHASE HPLC | |
|---|---|
| Fraction | Antithrombin activity [U/ml] |
| A | 667 |
| B | 843 |
| C | 435 |

TABLE 3-continued

SEPARATION BY REVERSED PHASE HPLC

| Fraction | Antithrombin activity [U/ml] |
| --- | --- |
| D | 274 |
| E | 2191 |
| F | 9684 |
| G | 2402 |
| H | 216 |
| I | 936 |
| J | 854 |

The amino-terminal sequence of the fractions containing thrombin-inhibiting activity was determined using a peptide sequencer (Applied Biosystems, Modell 477A). Table 4 shows the amino-terminal sequences of the main fractions E, F, G and J in Table 3.

TABLE 4

AMINO-ACID SEQUENCES OF THE HPLC FRACTIONS

| Fraction | SEQ ID NO | Amino-terminal sequence |
| --- | --- | --- |
| E | 4 | IRFGMGKVPCPDGEVGYTCDC (G) EX (I) |
| F | 5 | IRFGMGKVPXPDGEVGYTXDXGEKIXLYCQSXNDGQXS (G) (D) PKX |
| G | 6 | IXFGMGKVPCPDGEVGY (T) (C) (D) (C) (G) XX (I) |
| J | 7 | IXFGMGKVPCLDGEV (G) (Y) |

The amino acids indicated in parentheses have not been identified unambiguously. X is an amino acid which could not be identified. Peptide mapping of the isolated thrombin-inhibitory proteins To determine further partial amino-acid sequences, the fractions containing thombin-inhibiting activity were, after reduction and pyridyl ethylation (Huang et al., Biochemistry 28 (1989) 661–666), subjected to cleavage by the protease trypsin. The protein/protease ratio was 20–40 to 1.

The protease incubation was carried out at 37° C. for 4 hours in accordance with the manufacturer's instructions. The resulting peptide fragments were fractionated by reversed phase HPLC on a C-4 column (rp304®, BioRad). This was done, after the column had been washed with 0.5% by weight TFA in H$_2$O for 5 minutes, by use of a linear gradient from 0.1% by weight TFA in H$_2$O to 0.1% by weight TFA in 60% acetonitrile in 120 min. The peptides detected at 210 nm were collected separately and, after removal of the solvent by evaporation, analyzed in a gas-phase sequencer (Applied Biosystems Model 477A). FIG. 2 shows the separation of tryptic peptides obtained from digestion of fraction F (FIG. 1). Table 5 summarizes the detected amino-acid sequences.

TABLE 5

AMINO-ACID SEQUENCES OF FRACTION F AFTER TRYPSIN CLEAVAGE

| Fraction | SEQ ID NO | Amino-terminal sequence |
| --- | --- | --- |
| 2 | 8 | VPCPDGEVGYTCDCG |
| 2 | 9 | VPCP (D/F) GEVGYTCDCGX (N/D) ICL |
| 4 | 10 | ICLYGQSCNDGQCSGDPKPS (S) X |

X is any natural amino acid. Amino acids in parentheses could not be identified unambiguously. (D/F) means that both the amino acid Asp and Phe were detected at this position.

EXAMPLE 2

Determination of the inhibition of thrombin by the inhibitor

Thrombin (Boehringer Mannheim) was dissolved to a final concentration of 25 mU/ml in phosphate-buffered saline (PBS) (0.8 g/l NaCl; 0.2 g/l HCl; 0.144 g/l sodium phosphate; 0.2 g/l potassium phosphate, pH 7.5).

Chromozym TH (Boehringer Mannheim) was dissolved in 20 ml of H$_2$O/vial.

50 µl of thrombin solution and 100 µl of Chromozym plus 25 µl of sample or buffer were placed in the wells of a microtiter plate. The absorption at 405 nm was measured immediately thereafter at time 0 and after 30 minutes at 37° C. When the sample had a strong color of its own, another control without thrombin was treated as above.

The thrombin activity leads to liberation from the chromogenic substrate of a dye which absorbs at 405 nm. The inhibition of thrombin by a thrombin inhibitor is evident from a smaller increase in absorption at 405 nm and was quantified using a calibration plot.

EXAMPLE 3

Preparation of an affinity column with thrombin as ligand a) Coupling:

6.6 g of CNBr-activated Sepharose (Pharmacia) were washed with 200 ml of 1 mM HCl on a suction funnel. The gel was taken up in 100 mM NaHCO$_3$, 500 mM NaCl pH 8.3 and immediately mixed with 10000 units of thrombin (Sigma) in 100 mM NaHCO$_3$, 500 mM NaCl, pH 8.3.

The solution was carefully shaken at 4° C. for 24 hours.

b) Blocking:

The gel material was, after sedimentation, washed with 100 mMNaHCO$_3$, 500 mMNaCl, pH 8.3. The Sepharose was then incubated with 100 mM NaHCO$_3$, 500 mM NaCl, 1M ethanolamine pH 8.3 for 2 hours.

c) Preparation:

To remove unbound thrombin before use, the gel material in the column is washed once more with 20 column volumes of PBS pH 7.4.

EXAMPLE 4

Determination of the molecular weight by molecular sieve chromatography.

The product fractions from the thrombin-Sepharose chromatography were fractionated on a molecular sieve column (Superose 12, Pharmacia) to determine the apparent molecular weight of the purified thrombin inhibitors. The following chromatography parameters were used: flow rate 0.5 ml/min; detection 280 nm; fraction size 0.25 ml; buffer 20 mM phosphate-buffered saline (20 mM sodium phosphate, 0.15 M sodium chloride, pH 7.4).

The resulting chromatogram is shown in FIG. 3. The thrombin-inhibitory activity of the fractions was determined as described and entered on the chromatogram. The molecular weight of the inhibitors was determined by calibration of the column with standard proteins and was 11200±1000 dalton.

EXAMPLE 5

Determination of the molecular weight by tris/tricine SDS polyacrylamide gel electrophoresis.

(Literature: Analytical Biochemistry 166 (1987) 368–379 Tricine-Sodium Dodecyl Sulfate-Polyacrylamide Gel Electrophoresis for the Separation of Proteins in the range from 1–1000 kDa, Schägger, H. and von Jagow, G.)

For further characterization of the purified inhibitors, an aliquot corresponding to 5 μg was fractionated on a 16% tris/tricine gel (Bai GmbH, Bensheim). FIG. 4 shows the result after staining of the gel with Coomassie brilliant blue. The standards used here were marker proteins (Lanes 1 and 4) and recombinant hirudin (Lane 3). the molecular weight of the novel inhibitors (Lane 3) was found to be 5000±1000 dalton.

EXAMPLE 6

Preparation of a DNA sequence which codes for a thrombininhibitory protein.

a) Isolation of RNA and preparation of a cDNA bank

Total RNA from whole animals of the species Haemadipsa sylvestris was obtained by disintegration in guanidinium thiocyanate using materials from, and in accordance with the instructions of, the RNA Isolation Kit from Stratagene, La Jolla, Calif., USA (Catalog No. 200345).

The polyadenylated messenger RNA was selected from the abovementioned total RNA by oligo(dT) affinity separation. This process was carried out with materials from, and in accordance with the instructions of, the PolyATtract mRNA Isolation System from Promega, Madison, Wis., USA (Catalog No. Z5200).

cDNA was synthesized from polyadenylated messenger RNA using materials from, and in accordance with the instructions of, the ZAP-cDNA Synthesis Kit from Stratagene, La Jolla, Calif., USA (Catalog No. 200400) and was then packaged using materials from, and in accordance with the instructions of, the Uni-ZAP XR GigapackII Cloning Kit from Stratagene, La Jolla, Calif., USA (Catalog No. 237611) into lambda phages.

b) Preparation of oligonucleotide probes for the PCR

Peptides of the protein sequence described in Example 1 were used as starting material for the cloning of cDNA fragments by the polymerase chain reaction (PCR, see Molecular Cloning, 2nd Edition (1989), Sambrook, J. et al., CSH-Press, page 14.1 et seq.).

On the basis of the genetic code it is possible to deduce from the peptide sequence:
NH$_2$-Gly Met Gly Lys Val Pro Cys Pro (Pos.4–11) (SEQ ID NO: 11)
the nucleic acid sequence:
5'-GGA ATG GGN AAR GTN CCN TGY CC-3' (SEQ ID NO: 12)
and from the peptide sequence:
NH$_2$-Cys-Asp-Cys-Gly-Glu-Lys-Ile-Cys (Pos.19–26) (SEQ ID NO: 13)
the nucleic acid sequence:
5'-TGY GAY TGY GGN GAR AAR ATH TG-3' (SEQ ID NO: 14) of the coding DNA strand. Because of the known degeneracy of the genetic code, several nucleotides (N: A,C,G,T; Y: C,T; R: A,G; H: A,C,T) can be employed at some positions. This results in a mixture complexity of 256-fold for SEQ ID NO: 12 or 384-fold for SEQ ID NO: 14. The said sequences were synthesized as oligonucleotides.

The following oligonucleotides were additionally synthesized as 3' primers:
SEQ ID NO: 15:
5'-CGAGGGGGATGGTCGACGGAAGCGAC-CTTTTTTTTTTTTTTTTTTTT-3'; and SEQ IU NO: 16:
5'-CGAGGGGGATGGTCGACGG-3'; and SEQ ID NO: 17:
5'-GATGGTCGACGGAAGCGACC-3'.

The syntheses were carried out with an Applied Biosystems Type 360A DNA synthesizer. The oligonucleotides were, after removal of the protective groups, purified by gel electrophoresis on an acrylamide/urea gel.

c) Preparation of DNA templates for the PCR

5 μg of total RNA or 1 μg of poly(A)$^+$ RNA from the RNA preparation detailed under a) were converted with 1 μg of the oligonucleotide SEQ ID NO: 15:
5'-CGAGGGGGATGGTCGACGGAAGCGAC-CTTTTTTTTTTTTTTTTTTTT-3'
and using the enzyme reverse transcriptase into single-stranded cDNA (1° cDNA). This was carried out using the materials from, and in accordance with the instructions of, the SuperScript Preamplification System from Gibco BRL, Eggenstein, Germany (Catalog No. 8089SA). After completion of the reaction, the synthesis products were purified using the Geneclean II Kit from BIO 101, La Jolla, Calif., USA, to remove smaller molecules and excess oligonucleotides.

d) PCRs and cloning of a partial cDNA sequence

The polymerase chain reaction was carried out in accordance with known protocols (see Molecular Cloning, 2nd Edition (1989), Sambrook, J. et al., CSH Press, page 14.1 et seq.) using a DNA Thermal Cycler from Perkin Elmer. The principle of the nested primers described by Frohmann, M. A. et al. (Proc. Natl. Acad. Sci. USA 85 (1988) 8998–9002) was used with a modification of the method of Fritz, J. D. et al. (Nucl. Acids Res. 19 (1991) 3747).

Specifically, the 1° cDNA from c) was amplified with, in each case, 20 pmol of oligonucleotides of SEQ ID NO: 12 and SEQ ID NO: 16. The conditions for this were: 95° C. for 1 min; 55° C. for 2 min; 72° C. for 3 min for 35 cycles.

The PCR products were fractionated by electrophoresis on a 1.2% low melting agarose/TBE gel (TBE: 100 mM tris, 100 mM boric acid, 2 mM EDTA, pH 8.0).

About 10 slices were cut out of the gel over the entire length of the smear and were melted as separate fractions containing DNA fragments of increasing molecular mass.

Aliquots of these fractions were then used separately in a second PCR with, in each case, 20 pmol of oligonucleotides of SEQ ID NO: 14 and SEQ ID NO: 17. During this the agarose content never exceeded 1/10 of the volume of the PCR mixture. Reaction conditions: 95° C. for 1 min; 50° C. for 2 min; 72° C. for 3 min for 35 cycles.

The fractionation by gel electrophoresis of the products of the amplification of these fractions clearly revealed a reduction in the complex product spectrum of the first PCR to the extent that there was a defined band after the second PCR.

The PCR products selected in this way were eluted by standard methods. After subcloning into the EcoRV cleavage site of the pBluescriptKS vector and replication of the plasmid in E. coli DH5alpha, analysis of the sequence of a clone (SEQ ID NO: 18) showed an open reading frame of 39 amino acids (SEQ ID NO: 19) which agreed with the predicted protein sequence.

e) PCRs and cloning of the total coding region

To deduce the total cDNA sequence, another PCR amplification was carried out. The oligonucleotides:
5'-GGGGGGGTCGACGGATCCGTTACA-
GATAATTATTGCCAAAGC-3' (SEQ ID NO: 20), and
5'-CAGGAAACAGCTATGACC-3' (SEQ ID NO: 21)
were synthesized as primers for this reaction.

In this connection, SEQ ID NO: 20 is derived from the sequence shown in SEQ ID NO: 18; it corresponds to the sequence of the complementary strand in positions 158–180. The additional 18 nucleotides at the 5' end of SEQ ID NO: 20 are intended to reconstitute a SalI or BamHI cleavage site. Oligonucleotide SEQ ID NO: 21 corresponds to the sequence of the commercial reverse primer (Stratagene, La Jolla, Calif., USA) and is derived from sequences of the UniZAP XR lambda phage.

A PCR with these two oligonucleotides and an aliquot of the total phage lysate described in a) as template led to isolation of a cDNA sequence (SEQ ID NO: 22) which contains the complete coding region of the abovementioned thrombin inhibitor.

Specifically, this was done by boiling 10 µl of a high-titer phage lysate $10^9$–$10^{10}$ pfu/ml) of the Haemadipsa cDNA bank for 10 minutes and amplifying in a PCR reaction with, in each case, 20 pmol of oligonucleotides of SEQ ID NO: 20 and SEQ ID NO: 21. The conditions for this were: 95° C. for 1 min; 55° C. for 2 min; 72° C. for 3 min for 35 cycles; total volume 100 µl.

The PCR product analyzed by gel electrophoresis was eluted by standard methods. After subcloning into the EcoRV cleavage site of the pBluescriptKS vector and replication of the plasmid in E. coli DH5alpha, analysis of the sequence of a clone (SEQ ID NO: 22) showed an open reading frame of 77 amino acids (SEQ ID NO: 23) which agreed with the predicted protein sequence.

f) Heterologous expression of the thrombin inhibitor

To prepare the recombinant thrombin inhibitor, initially amino-acid sequence SEQ ID NO: 23 was translated back from position 1 to 57 into a nucleotide sequence taking account of the codon selection typical of E. coli. The following codon selection was used for this: Arg: CGT Asn: AAC Asp: GAC Cys: TGC Gln: CAG Glu: GAA Gly: GGT Ile: ATC Leu: CTG Lys: AAA Met: ATG Phe: TTC Pro: CCG Ser: TCC Thr: ACC Tyr: TAC Val: GTT The double-stranded nucleotide sequence was prepared by chemical oligonucleotide synthesis and enzymatic ligation by known processes. The nucleotide sequence was provided with XmnI- and BamHI-compatible ends and cloned into the E. coli expression vector pMAL-p2 (New England Biolabs).

The recombinant plasmid was used to transfect E. coli DH 5α cells. The thrombin inhibitor was prepared as fusion protein with maltose binding protein and isolated and purified in accordance with the statements of the vector manufacturer.

The concentration of the thrombin inhibitor, which undergoes periplasmic expression, was 1250 units per liter of culture medium.

Figure 1:
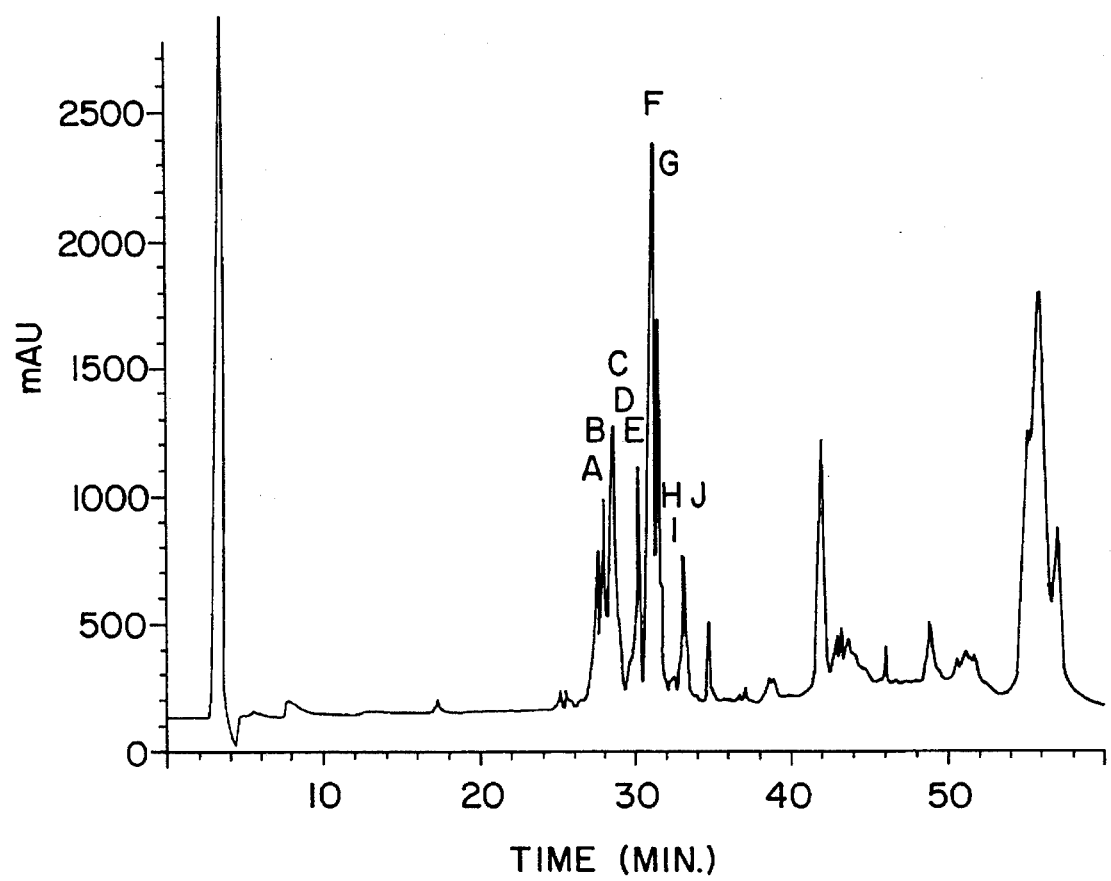
FIG. 1: Fractionation of the product fraction ($P_3$) from the thrombin-Sepharose by reversed phase HPLC on a BioRad rp 304® column. The sample was dissolved in 0.1% by weight trifluoroacetic acid in water and, after washing with 0.1% by weight trifluoroacetic acid in water for 5 minutes, fractionated using a linear gradient from 0.1% by weight TFA in water to 0.1% by weight TFA in acetonitrile and 1%/min. Fractions with thrombin-inhibitory activity (A-J) were collected separately.
Figure 2:
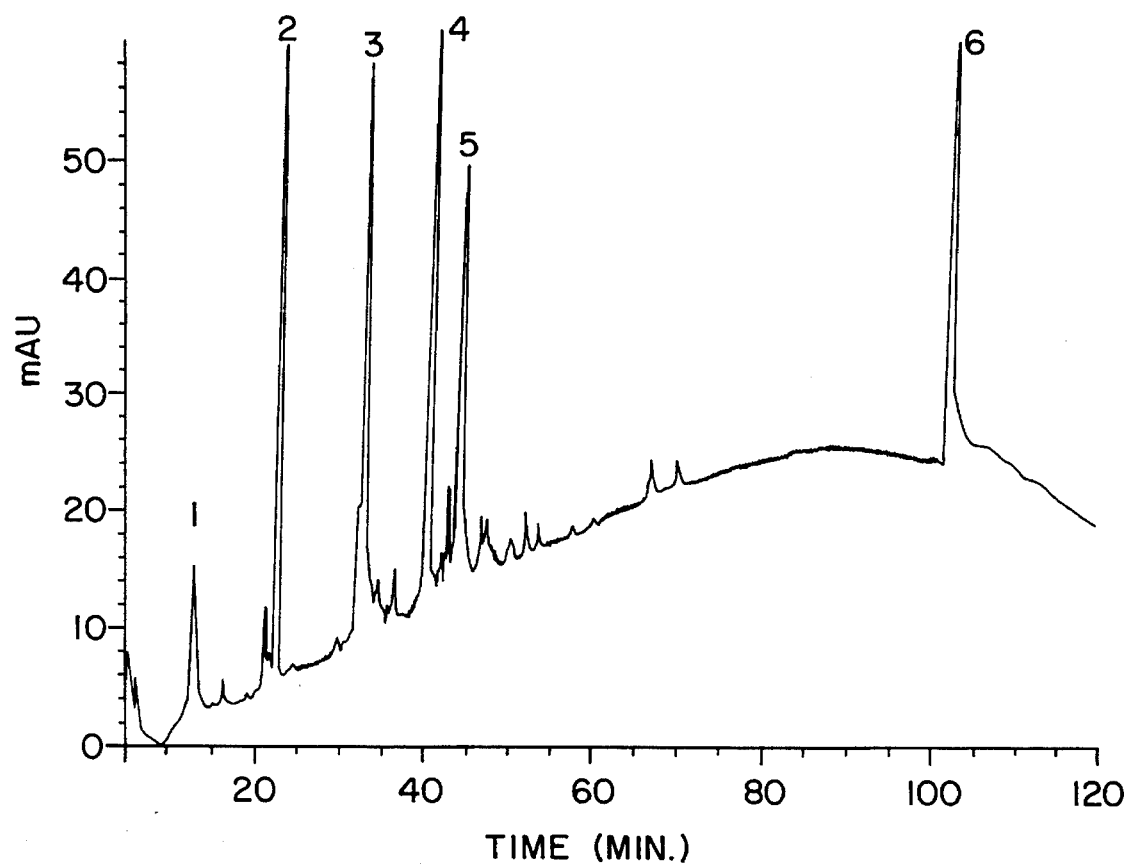
FIG. 2: Fractionation of tryptic fragments of the product fraction F (FIG. 1) by reversed phase HPLC. The peptide fragments obtained from the cleavage were fractionated, after the column had been washed with 0.1% by weight TFA in water for 5 min, using a linear gradient to 0.1% strength TFA in 60% acetonitrile in 120 min. Detection took place at 210 nm, and the resulting fractions (1–6) were analyzed, after the solvent had been evaporated off, in a gas-phase sequencer.
Figure 3:
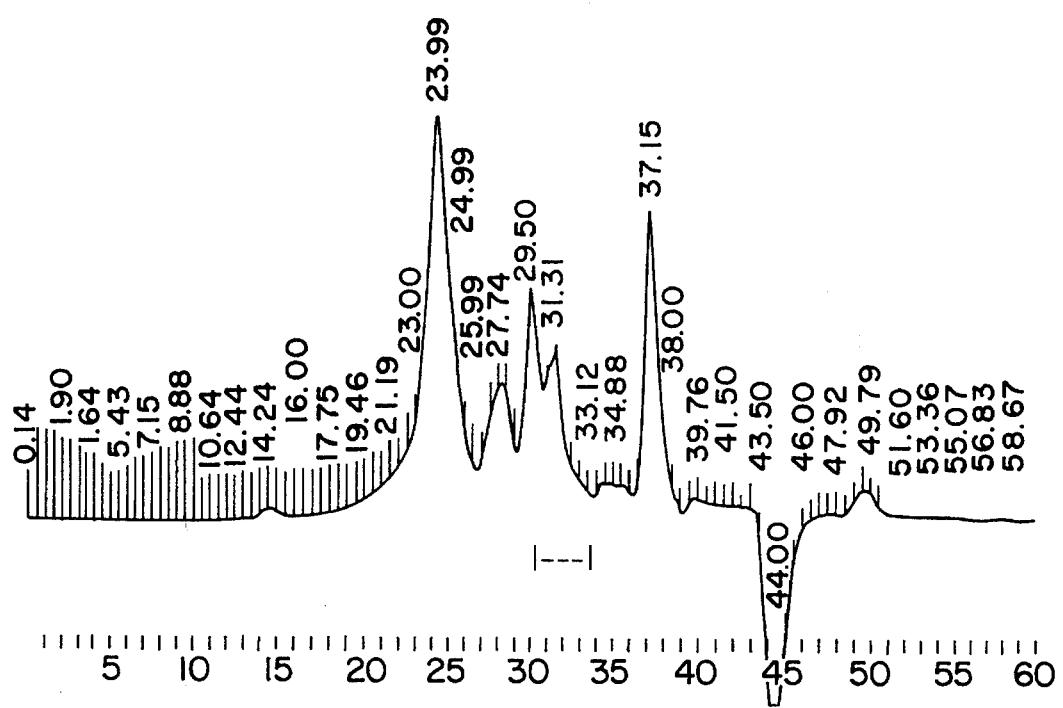
FIG. 3: Determination of the apparent molecular weight of the thrombin inhibitors with a molecular sieve column (Superose 12, Pharmacia). Sample: product fraction from the thrombin-Sepharose; flow rate: 0.5 ml/min; buffer: 20 mM sodium phosphate, 0.15 M sodium chloride, pH 7.4); fraction size 250 µl; detection: 280 nm. The fractions containing thrombin-inhibitory activity are indicated on the chromatogram (l—l).
Figure 4:
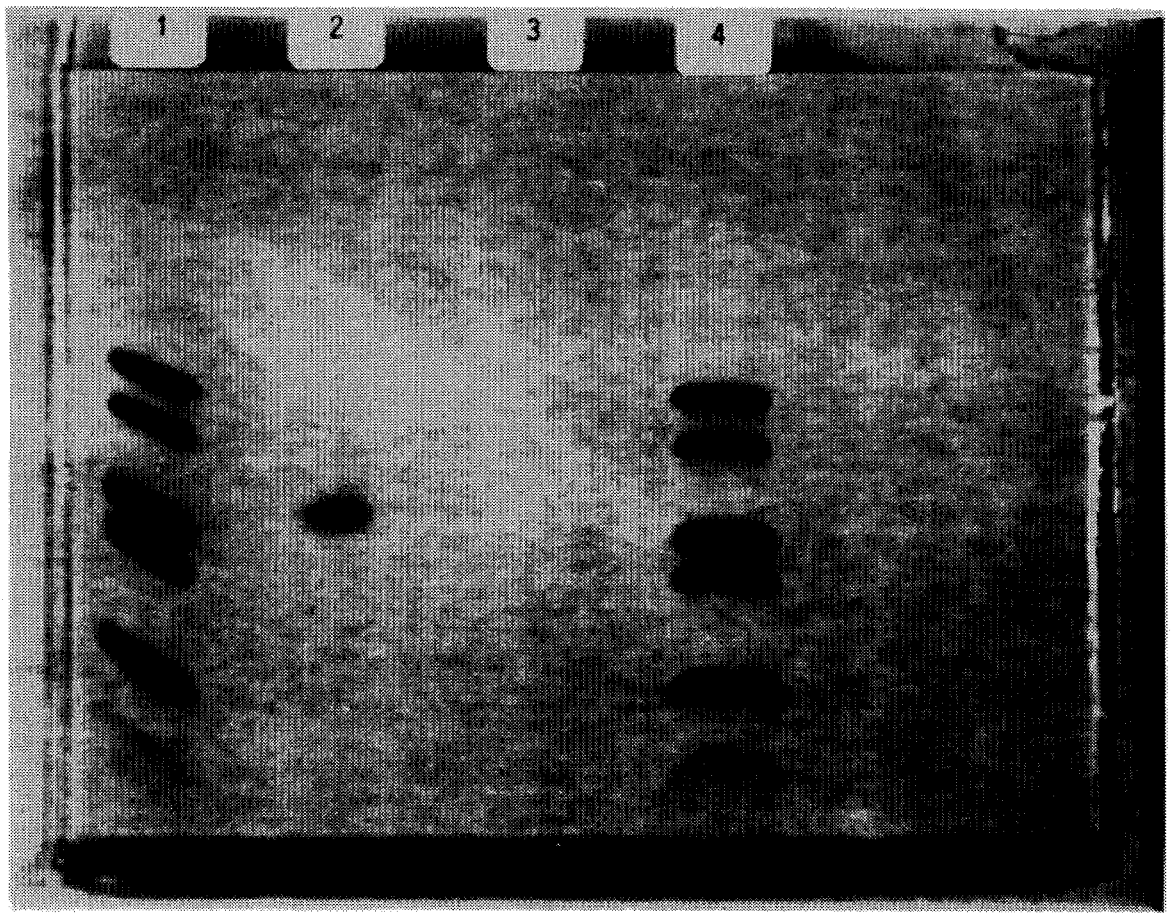
FIG. 4: Determination of the apparent molecular weight of the thrombin inhibitor by tris/tricine SDS gel electrophoresis. An aliquot equivalent of 5 µg was fractionated on a 16% tris/tricine gel (Bai-GmbH, Bensheim) and visualized by staining with Coomassie brilliant blue (Lane 3). The molecular weight was found with the aid of commercial molecular weight markers (Lanes 1 and 4) to be 5000±1000 dalton. Lane 2 was recombinant hirudin.

We claim:

1. A protein with thrombin-inhibitory activity from terrestrial leeches of the genus Haemadipsa with the amino acid sequence Ile-Arg-Phe-Gly-Met-Gly-Lys-Val-pro- Cys-Pro-Asp-Gly-Glu-Val-Gly-Tyr-Thr-Cys-Asp-Cys-Gly-Glu-Lys-Ile-Cys-Leu-Tyr-Gly-Gln-Ser-Cys-Esn-Asp-Gly-Gln-Cys- Ser-Gly-Asp-Pro-Lys-Pro-Ser-Ser-Glu-Phe-Glu-Glu-Phe-Glu- Ile-Asp-Glu-Glu-Glu-Lys (SEQ ID NO: 1) or an amino-acid sequence which is obtained by C-terminal truncation of SEQ ID NO: 1 by from one to twelve amino acids.

2. A protein as claimed in claim 1 with the sequence SEQ ID NO: 2.

3. A DNA sequence which codes for a protein with thrombin-inhibitory activity and which is selected from the group consisting of a) DNA sequence of SEQ ID NO: 22, b) DNA sequences which codes for the protein of claim 1 or 2.

4. An expression vector which contains a DNA sequence as claimed in claim 3.

5. The method of using proteins which are encoded by DNA sequences as claimed in claim 3 for treatment of thromboses or arterial occulsions.

6. A pharmaceutical composition containing one or more proteins which are encoded by DNA sequences as claimed in claim 3, and another coagulation-inhibiting factor.

7. A pharmaceutical composition as claimed in claim 6, wherein a hirudin is used as another coagulation-inhibiting factor.

* * * * *

UNITED STATES PATENT AND TRADEMARK OFFICE
CERTIFICATE OF CORRECTION

PATENT NO.: 5,455,181

DATED: October 3, 1995

INVENTOR(S): STRUBE et al.

It is certified that error appears in the above-identified patent and that said Letters Patent is hereby corrected as shown below:

Column 22, claim 3, line 1, "sequences" should be --sequence--.

Signed and Sealed this

Sixteenth Day of January, 1996

Attest:

BRUCE LEHMAN

Attesting Officer     Commissioner of Patents and Trademarks